US00PP12274P2

(12) United States Plant Patent
Utecht

(10) Patent No.: US PP12,274 P2
(45) Date of Patent: Dec. 11, 2001

(54) GERANIUM PLANT NAMED 'FISTANGOLI'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,110

(22) Filed: Jun. 1, 1999

(51) Int. Cl.[7] ..... A01H 5/00
(52) U.S. Cl. ..... Plt./329
(58) Field of Search ..... Plt./329, 330, 325

(56) References Cited

FOREIGN PATENT DOCUMENTS

| | | |
|---|---|---|
| 98-1367 | 4/1998 | (CA) . |
| 98-26-1429 | 4/1998 | (CH) . |
| PEL 1365 | 9/1996 | (DE) . |
| 97/0963 | 9/1997 | (EP) . |
| 470 | 12/1998 | (PL) . |

OTHER PUBLICATIONS

UPOV–ROM GTIM Computer Database 1999/02, GTI Jouve Retrieval Software, citation for 'Fistangoli', 1996–1998.*

Licensing agreement, http://www.sicasov.com/baremes/f–fl9899.htm., 1998/1999.*

Pelargonium 1998, Pelfi Fischer, Hillscheid Germany, p. 9 (1998/1999).

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of geranium plant named 'Fistangoli', as described and illustrated, and particularly characterized by the combined features of bright-purple flower color; huge umbels on strong, dark-red peduncles borne well above the foliage; dark green foliage with weak zonation; and low, compact plant habit.

1 Drawing Sheet

BACKGROUND OF THE INVENTION

The present invention comprises a new and distinct cultivar of geranium plant botanically known as *Pelargonium zonale*, and hereinafter referred to by the cultivar name 'Fistangoli'.

'Fistangoli' is a product of a planned breeding program which had the objective of creating new geranium varieties with the bright purple flower color known from the commercial variety 'Kardinal' (unpatented), in combination with semi-double flowers and low, compact plant habit.

'Fistangoli' was originated from a hybridization made by the inventor, Angelika Utecht, in a controlled breeding program in Galdar, Gran Canaria, Spain, in 1993. The female parent was a hybrid seedling, designated no. 876/2, derived from a cross of a tetraploid line of 'Kardinal' with a hybrid seedling of unknown parentage, designated no. 2198/2, which was characterized by pink semi-double flowers, dark-green foliage and compact growth. 'Kardinal' has single purple flowers with orange markings, medium green, nicely zoned foliage and vigorous growth, but poor branching characteristics. The male parent of 'Fistangoli' was the commercial variety 'Americana Violet' (U.S. Plant Pat. No. 8,750), which was characterized by purple flowers, light to medium-green foliage with weak zonation, and compact growth.

'Fistangoli' was selected as one flowering plant within the progeny of the stated cross by the inventor, Angelika Utecht, in 1994 in a controlled environment in Galdar, Gran Canaria, Spain.

The first act of asexual reproduction of 'Fistangoli' was accomplished when vegetative cuttings were taken from the initial selection in autumn 1994 in a controlled environment in Galdar, Gran Canaria, Spain by Angelika Utecht. Horticultural examination of plants grown from these cuttings, initiated in May 1996 in Hillscheid, Federal Republic of Germany, and continuing thereafter, has demonstrated that the combination of characteristics as herein disclosed for 'Fistangoli' are firmly fixed and are retained through successive generations of asexual reproduction.

BRIEF DESCRIPTION OF THE INVENTION

The following traits have been repeatedly observed and are determined to be basic characteristics of 'Fistangoli', which in combination distinguish this geranium as a new and distinct cultivar:

1. Bright purple-colored, semi-double flowers;
2. Large inflorescence, borne well above the foliage;
3. Dark-green foliage with weak zonation;
4. Weak growth, and low, compact plant habit; and
5. Early to medium flowering response.

'Fistangoli' has not been observed under all possible environmental conditions. The phenotype of the new cultivar may vary significantly with variations in environment such as temperature, light intensity and daylength without any change in the genotype of the plant. The following observations, measurements, and comparisons describe plants grown in Hillscheid, Germany, and in Langley, British Columbia, Canada, under greenhouse conditions which approximate those generally used in commercial practice.

Of the many commerical cultivars known to the present inventor, the most similar in comparsion to 'Fistangoli' is the variety 'Fisdino' (U.S. Plant Pat. No. 8,761). In comparison to 'Fisdino', 'Fistangoli' has a similar flower color, but different markings on its petals, larger inflorescence, and more compact plant habit. 'Fistangoli' has dark-green foliage whereas 'Fisdino' has medium-green foliage.

BRIEF DESCRIPTION OF THE DRAWING

The accompanying color photographic drawing shows typical flower and foliage characteristics of 'Fistangoli' with colors being as true as possible will illustrations of this type.

DETAILED BOTANICAL DESCRIPTION

The measurements were taken in Langley, British Columbia, Canada, on May 26, 1998, 10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheid, Germany.

Classification:

*Botanical.*—A hybrid of the species *Pelargonium zonale L'Hérit.*

*Commercial.*—Zonal geranium, cv. 'Fistangoli'.

Inflorescence:

*Umbel.*—Shape: Flat, semi-spherical and very wide. Average diameter: 133 mm. Average depth: 65 mm. Peduncle length: 15.7 mm. Peduncle color: Dark-red, RHS 183 A. Peduncle texture: Thin, slightly rough or velvety with weak pubescence. Pedicel length: 29 mm. Pedicel Color: Greenish, RHS 137 D, at the base; light brownish-red, approximately RHS 178 C to 179 A, in the middle; darker red, near RHS 178 A, at the upper end. Number of flowers per umbel: Approximately 40. Lastingness of the individual umbel: Large, wide and consisting of many individual flowers that open one by one so the umbel lasts longer than the average zonal variety, lasting approximately 14 days in greenhouse conditions in spring at a temperature of 18° C.

*Corolla.*—Average diameter: 49 mm. Form: Semi-double. Shape: Nearly round, with an open middle. Number of petals: 7–9. Number of petaloids: 1–2. Color (general tonality from a distance of three meters): Bright purple. Color of upper petals: RHS 66 B. Markings of upper petals: Salmon-red hue, near RHS 50 A, at the base. Color of lower petals: RHS 66 B, without any markings. Color of lower surface of petals: RHS 66 B–74 B. Color of sepals: Light green, RHS 137 D, basal part is reddish. Texture of sepals: Smooth to slightly velvety, with weak pubescence. Number of sepals: 5.

*Bud (immediately before unfolding of the petals).*—Shape: Elliptical. Color (sepals): Light to medium-green, RHS 143 A. Color (petals): Red-purple, approximately RHS 57 A–66 A. Length: Approximately 22 mm. Width: Approximately 11 mm.

*Reproductive organs.*—Androecium: 7 fertile anthers, whitish to light-pink filaments, yellow-orange pollen. Gynoecium: 5–6 lobed stigma, purple stigma and style. Fertility/seed set: Occasionally, very few seeds.

*Spring flowering response period.*—In Hillscheid, Germany, in 1998, plants had on average 0.9 flowers opened 1 week after planting of unrooted cuttings.

*Outdoor flower production.*—The number is slightly under average, due to the large size of the inflorescence.

*Blooming habit.*—Continuous flowering from about May to mid-September; after which flowering may be poor depending on general conditions and light intensity. There is no noticeable fragrance apart from the slightly aromatic scent that can be noticed when flowers are crushed.

*Lastingness of the individual bloom.*—The floret does not drop its petals easily (no shattering) and is not very susceptible to getting burned/scorched by the sun, so the flowers last approximately 8–9 days in greenhouse conditions in spring at a temperature of 18° C.

*Durability.*—Good shatter resistance, relatively good rain resistance.

Plant:

*Foliage.*—Form: Kidney-shaped, with an open base. Margin: Bicrenated, wavy. Size of leaf: 80 mm wide. Texture: Slightly velvety and dull (not glossy). Color of upper surface: Dark-green, approximately RHS 137 A. Color of lower surface: RHS 137 C. Color of zonation: Very weak, brown, approximately RHS 166 A, or only a darker shade of green, may be invisible in summer. Tolerance of botrytis: Average.

*General appearance and form.*—Internode length: 10–15 mm. Branching pattern: 3.7 naturally-occuring branches. Size of foliage: Approximately 13.2 cm high and 27 cm in diameter.

I claim:

1. A new and distinct cultivar of geranium plant named 'Fistangoli', as described and illustrated.

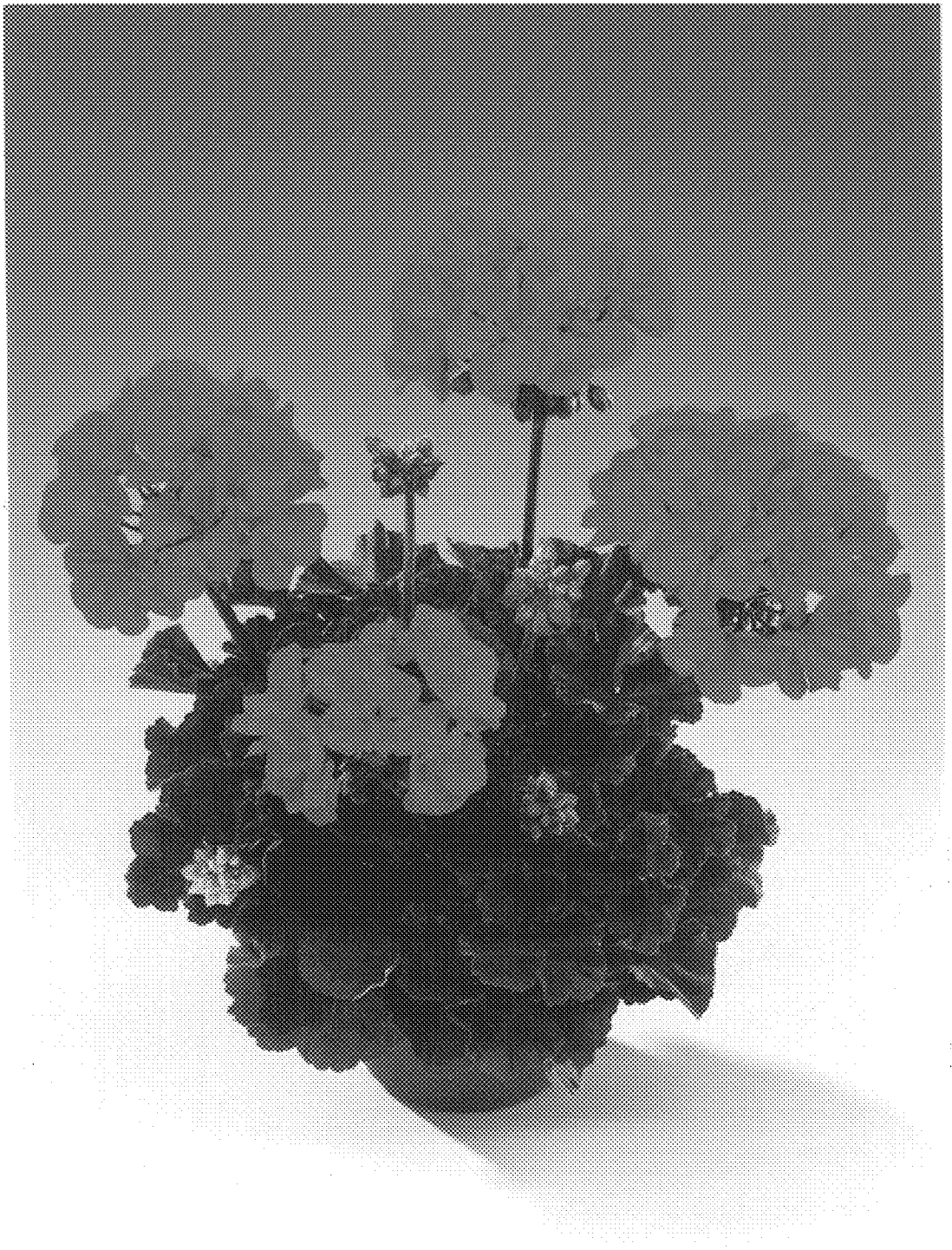

* * * * *